(12) United States Patent
Wang et al.

(10) Patent No.: US 9,101,376 B2
(45) Date of Patent: Aug. 11, 2015

(54) ULTRASONIC IMAGING MICROWAVE THERAPEUTIC APPARATUS

(71) Applicant: Beijing TransEasy Medical Tech Co., Ltd., Beijing (CN)

(72) Inventors: Xiaoping Wang, Beijing (CN); Jinxiu Huang, Beijing (CN); Qingyi Meng, Beijing (CN); Jie Sun, Beijing (CN); Chongliang Fang, Beijing (CN)

(73) Assignee: Beijing TransEasy Medical Tech Co., Ltd., Beijing (CN)

( * ) Notice: Subject to any disclaimer, the term of this patent is extended or adjusted under 35 U.S.C. 154(b) by 228 days.

(21) Appl. No.: 13/726,037

(22) Filed: Dec. 22, 2012

(65) Prior Publication Data

US 2013/0211257 A1 Aug. 15, 2013

(30) Foreign Application Priority Data

Feb. 10, 2012 (CN) .......................... 2012 1 0028956

(51) Int. Cl.
*A61B 18/18* (2006.01)
*A61B 8/00* (2006.01)
*A61B 8/08* (2006.01)
*A61B 8/13* (2006.01)
*A61N 5/04* (2006.01)
*A61B 18/00* (2006.01)

(52) U.S. Cl.
CPC .............. *A61B 18/1815* (2013.01); *A61B 8/13* (2013.01); *A61B 8/463* (2013.01); *A61B 8/488* (2013.01); *A61B 8/54* (2013.01); *A61B 8/546* (2013.01); *A61B 2018/00404* (2013.01); *A61B 2018/00982* (2013.01); *A61N 5/04* (2013.01)

(58) Field of Classification Search
None
See application file for complete search history.

(56) References Cited

U.S. PATENT DOCUMENTS

| | | | | |
|---|---|---|---|---|
| 5,762,066 A | * | 6/1998 | Law et al. | 600/439 |
| 7,630,418 B2 | * | 12/2009 | Franjic et al. | 372/21 |
| 2010/0185087 A1 | * | 7/2010 | Nields et al. | 600/439 |
| 2012/0143180 A1 | * | 6/2012 | Lee et al. | 606/33 |
| 2013/0102862 A1 | * | 4/2013 | Mercader et al. | 600/317 |

FOREIGN PATENT DOCUMENTS

WO WO 2007025198 A2 * 3/2007 ............. A61B 18/18

* cited by examiner

*Primary Examiner* — Long V Le
*Assistant Examiner* — Kevin Pontius

(57) ABSTRACT

An ultrasonic imaging microwave therapeutic apparatus includes a microwave radiation probe, a microwave generating unit, a laser generating unit, a color Doppler ultrasound imaging unit, and a microcomputer control unit. The microcomputer control unit outputs the microwave power control signal to control and adjust the power of the microwave generating unit. The microcomputer control unit outputs the laser control signal to control the switch-on/off of the laser generating unit. The advantages of using the therapeutic apparatus to treat the lower extremity varicose vein disease are as follows. The closure of the varicose vessel is accurate, firm, and thorough. The effect is definite. The traumas for patients are small. The pain of patients is light. The intraoperative bleeding is less. The recovery of patients is rapid. It is difficult to form deep vein thrombosis, can accurately treat the diseased blood vessel and simultaneously instantly verify the effect of the surgery.

17 Claims, 3 Drawing Sheets

ULTRASONIC IMAGING MICROWAVE THERAPEUTIC APPARATUS

BACKGROUND OF THE PRESENT INVENTION

1. Field of Invention

The present invention relates to a radiotherapy apparatus, and more particularly to a microwave radiation therapeutic apparatus which is adapted but not limited to treat the lower extremity varicose vein, and is especially adapted for treating the severe varicose vein with leg ulcer. Furthermore, it is also adapted for the treatment of the superficial hemangioma.

2. Description of Related Arts

The lower extremity varicose vein, which can be diagnosed and treated in vascular surgery, general surgery and TCM (Traditional Chinese Medicine) surgery, is also known as primary lower extremity venous insufficiency and belongs to lower extremity venous reflux disease. It has higher incidence and appears symptomatic lower extremity venous insufficiency in about 10-15% of adult males and 20-25% of adult females. Classified from anatomy, the lower extremity venous system consists of the superficial venous system, the deep venous system, and the communicating venous system. A variety of factors, which lead to venous valve insufficiency, weak venous wall and lasting elevated intravenous pressure of the above-mentioned systems, may be pathogenic, thus the pathological changes and clinical manifestations will appear. This disease mostly happens to the person engaged in prolonged standing and squatting work, and the person with high-intensity physical activity. However, pregnancy, chronic cough, long-term constipation and so on can also cause the lasting elevated intravenous pressure, thereby easily leading to the varicose vein symptoms. Moreover, about 70% patients with this disease have a genetic predisposition. The concrete manifestations are lower extremity meandering expansion and earthworm-like superficial varicose vein tortuosity, which are more obvious for calf than thigh, more obvious after standing, and will be reduced or disappear after lifting a leg. Simultaneously, affected limb soreness, pain, numbness and other abnormal sensations appear. In the early period of this disease, affected limb soreness, heaviness and hypodynamia appear, or even pain, which are obvious while standing and can be reduced after walking, in supine position or while elevating the limb. In the late period of this disease, due to congestion, skin nutritional disorders are commonly seen, thereby causing calf atrophoderma, desquamation, itching, pigmentation, the subcutaneous tissue of the skin induration, thrombus, phlebitis, eczema, and chronic ulcer (which is commonly known as "old rotten feet"). It is possible for refractory ulcer to have a carcinogenesis.

Currently, the domestic traditional treatment method is the surgical treatment which has been about more than 100 years of history. It mainly includes large (small) saphenous vein high ligation, communicating branch ligation, and large (small) saphenous vein and varicose vein stripping surgery. The surgery is mainly divided into three steps of high-ligating the large or small saphenous vein, stripping the varicose vein, and ligating and cutting off the perforating vein. Due to the shortcomings of more incisions, major traumas, heavy bleeding, slow recovery, relatively more postoperative complications, large infection probability, and large operative risk from the surgery, it is not easy for the patients to accept the surgery. Therefore, in recent years, the surgical treatment has been gradually replaced by the minimally invasive surgical treatment method. At present, the popular minimally invasive surgery at home and abroad mainly includes: transilluminated powered phlebectomy (TIPP), endo venous laser treatment (EVLT), endo venous radio frequency treatment and subfascial endoscopic perforator surgery (SEPS).

In 1998, it was firstly reported by Carlos et al. that applying the endo venous laser to treat the lower extremity varicose large saphenous vein. After 1999, it was successively reported the success experiences of applying the endo venous laser to treat the lower extremity varicose large saphenous vein by other scholars. In 2000, the endo venous laser treatment was firstly introduced to Shanghai of China. It has been proved, by Proebstle et al., that the mechanism of treating the lower extremity varicose large saphenous vein by EVLT is: under the thermal effect of the laser, the endovenous blood boils for generating the steam foam, so as to widely damage the vascular endothelial cell and intima for inducing the formation of venous throughout thrombosis and closing the vein, thereby achieving the therapeutic effect. The disadvantages of the existing minimal invasive surgery are as follows. (1) Due to different physical energy, the closure of the diseased blood vessel is not firm enough, the diseased blood vessel is relatively easy to recur, and the thrombus occurs. (2) The indications are limited, the existing minimal invasive surgery is adapted for lighter illness, and can not simultaneously treat the leg ulcer caused by perforating venous insufficiency. (3) The operation is tedious. (4) The laser machine is just a single machine without timely monitoring of color Doppler ultrasound, the treatment is blind, and the effect can not be timely detected. (5) The equipment is expensive.

SUMMARY OF THE PRESENT INVENTION

To overcome the above-mentioned shortcomings of the existing minimal invasive surgery treating the lower extremity varicose vein disease, the present invention provides an ultrasonic imaging microwave therapeutic apparatus. By the therapeutic apparatus of the present invention, the lower extremity varicose vein disease can be conveniently, directly and effectively treated. The product of the present invention combines the treatment with the real-time monitoring as a whole for widening the indications of implementing the microwave endovascular treatment technology. These indications include large saphenous varicose vein, small saphenous varicose vein, gobbet-shaped varicose vein, superficial hemangioma, and perforating venous insufficiency with lower limb ulcer. The present invention is further adapted for elderly patients with high blood pressure, heart disease, emphysema and other comorbidities. Moreover, it is adapted for patients with calf vein ulcer and skin infection.

Accordingly, in order to solve the above technical problem, the present invention adopts the technical solution as follows.

An ultrasonic imaging microwave therapeutic apparatus, comprises:

a microwave radiation probe, comprising a front probe part, a rear probe part and a probe interface part, wherein a microwave emission hole is provided at the front probe rear, and a laser cursor is provided at the rear probe part;

a microwave generating unit comprising a microwave generator, wherein a power output of the microwave generating unit is connected with the probe interface part to provide a microwave signal for ablation treatment of lower extremity varicose vein;

a laser generating unit for providing a laser signal which is used to identify a wavelength range of visible light of the microwave probe;

a color Doppler ultrasound imaging unit, adapted for obtaining a treatment image of a tissue to be treated, comprising a color Doppler ultrasound host and a color Doppler ultrasound control panel; and a microcomputer control unit, wherein the microcomputer control unit outputs a microwave power control signal to control and adjust a power of the microwave generating unit, the microcomputer control unit outputs a laser control signal to control a switch-on/off of the laser generating unit.

Preferably, in the ultrasonic imaging microwave therapeutic apparatus provided by the present invention, the microwave generating unit comprises a microwave signal generator, a power control time adjusting circuit, an impedance matcher, a driving circuit, a power splitter, a plurality of power amplifiers, a power combiner, an isolator and a power tracking detection circuit. The working principle of the microwave generating unit is as follows. A microwave signal generated by the microwave signal generator is inputted into the power control time adjusting circuit, an output power is adjusted by the microwave power control signal from the microcomputer control unit and received by the power control time adjusting circuit, an output of the power control time adjusting circuit is connected with the impedance matcher to have an impedance matching for the inputted microwave signal, an output of the impedance matcher is connected with the driving circuit, a signal from the impedance matcher is pre-amplified by the driving circuit and then sent to the power splitter, the power signal is divided into multi-channel signals by the power splitter and then respectively sent to a plurality of power amplifiers for amplifying, the amplified power is synthesized by the power combiner, the synthesized power is outputted by a coaxial output terminal of the isolator, a microwave power output terminal of the isolator is connected with the power tracking detection circuit, the power tracking detection circuit outputs an output power detection signal, a reflected power detection signal, an over current signal and an over voltage signal.

Preferably, in the ultrasonic imaging microwave therapeutic apparatus provided by the present invention, the laser generating unit comprises an InGaAs infrared laser pump, and a laser cavity, wherein a laser medium and a nonlinear optical crystal are provided within the laser cavity along a same axis, the laser medium is $YVO_4$ crystal doped with $Nd^{3+}$, wherein a doping concentration of $Nd^{3+}$ is 2.5-7.2 at %, and the nonlinear optical crystal is KTP crystal. The working principle of the laser generating unit is as follows. Under the effect of infrared pump laser with the wavelength of 807 nm along the incident direction, the laser medium generates the fundamental laser with the wavelength of 1340 nm, and then makes the sum-frequency effect with the pump laser in the KTP crystal for generating green laser with the wavelength of about 504 nm. The green laser passes through the port and is transformed to the rear probe part of the microwave radiation probe via the optical fiber for identifying the position of the microwave radiation probe.

Preferably, in the ultrasonic imaging microwave therapeutic apparatus provided by the present invention, the rear probe part of the microwave radiation probe has a hollow structure, a wire for a transmission of microwave and a cable for a transmission of laser are provided within the rear probe part of the microwave radiation probe, the rear probe part of the microwave radiation probe is sealedly connected with a conduit with the wire and the cable, the conduit is connected with the probe interface part, a laser interface connected with a port of the laser generating unit and a microwave interface connected with a coaxial output terminal of the microwave generating unit are provided at the probe interface part.

Preferably, in the ultrasonic imaging microwave therapeutic apparatus provided by the present invention, a temperature sensor is located within the hollow structure of the rear probe part of the microwave radiation probe, a temperature signal transmission line is located within the conduit, and a temperature signal interface is provided at the probe interface part.

Preferably, in the ultrasonic imaging microwave therapeutic apparatus provided by the present invention, the microcomputer control unit comprises a master microprocessor, a power control microprocessor, and a temperature measurement microprocessor, wherein the master microprocessor is connected with the power control microprocessor and the temperature measurement microprocessor via a communication interface COM.

Preferably, in the ultrasonic imaging microwave therapeutic apparatus provided by the present invention, the output power detection signal and the reflected power detection signal of the microwave generating unit are transformed by an A/D converter, and then sent to the power control microprocessor, the over current signal and the over voltage signal of the microwave generating unit are inputted into the power control microprocessor, a power control signal of the microwave generating unit comes from an output of the D/A converter connecting with the power control microprocessor, a value of the power control signal is obtained by the power control microprocessor according to a value of the output power detection signal, the reflected power detection signal, the over current signal and the over voltage signal are processed by the power control microprocessor, and then inputted into the master microprocessor via the communication interface, and an alarm circuit is started by the master microprocessor for generating an alarm signal.

Preferably, in the ultrasonic imaging microwave therapeutic apparatus provided by the present invention, a temperature signal sensed by the temperature sensor is sent to a signal amplifier, an output of the signal amplifier is transformed by the A/D converter and then sent to the temperature measurement microprocessor, a temperature value outputted by the temperature measurement microprocessor is displayed by a status display.

Preferably, in the ultrasonic imaging microwave therapeutic apparatus provided by the present invention, the master microprocessor is further connected with a keyboard, the status display, the alarm circuit and a memory, wherein the keyboard is adapted for inputting a control instruction to the master microprocessor, the status display is adapted for displaying a working state, the alarm circuit is adapted for generating the alarm signal, and the memory is adapted for storing set values and temporary data at work.

Preferably, in the ultrasonic imaging microwave therapeutic apparatus provided by the present invention, the microwave radiation probe is a single-use microwave radiation probe, a unique identification code chip is located within the hollow structure of the rear probe part of the microwave radiation probe, the unique identification code chip is connected with the microcomputer control unit by the communication interface, the microcomputer control unit judges whether the microwave radiation probe is used by the unique identification code sensor. The repeated use of the microwave radiation probe can be effectively avoided by the unique identification code chip.

The treatment method using the ultrasonic imaging microwave therapeutic apparatus of the present invention is simply described as follows. The saphenous vein at the ankle of the affected limb or the groin is punctured or cut under anaesthesia. The microwave radiation probe is placed into the vessel. According to the width of the diameter of the vein of the affected limb, fat and thin body, the appropriate microwave emission power and coagulation time (within several seconds) are chosen to make the coagulation closing of the main vein. The lower extremity varicose tributary vein and the varicose vein group are closed via the short probe needle by skin multi-point venipuncture coagulation. For patients with perforating venous insufficiency (or leg ulcer), the short probe needle is used through the skin or superficial varicose vein (or the normal skin around the ulcer) to puncture for entering the diseased perforating vein, the perforating vein is coagulated and closed. Under color Doppler ultrasound, the treatment status and the closure effect of the varicose vein and the perforating vein are instantly fully monitored. Patients can be cured by a minimally invasive surgery.

Compared with the prior art, the present invention has the following beneficially technical effects. Using the ultrasonic imaging microwave therapeutic apparatus of the present invention to treat the lower extremity varicose vein disease, the closure of the varicose vessel is accurate, firm, and thorough, the effect is definite, the trauma for patients is small, the pain of patients is light, the intraoperative bleeding is less, the recovery of patients is rapid, it is difficult to form deep vein thrombosis and safe, the operation is simple, no obvious complication occurs. Under the full monitor of color Doppler ultrasound, the implementation of the minimally invasive surgery is capable of accurately treating the diseased blood vessel, and simultaneously instantly verifying the effect of the surgery.

These and other objectives, features, and advantages of the present invention will become apparent from the following detailed description, the accompanying drawings, and the appended claims.

Figure 1:
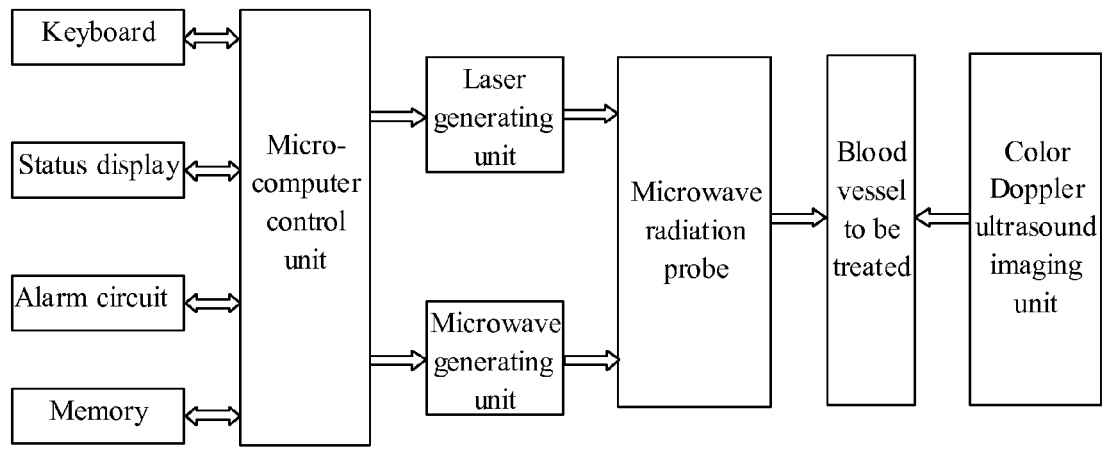
FIG. 1 is a block diagram of an ultrasonic imaging microwave therapeutic apparatus according to a preferred embodiment of the present invention.

In the drawings, 31—resonant cavity input lens; 32—nonlinear optical crystal; 33—laser medium; 34—resonant cavity output lens; 35—output direction; 71—front probe part; 72—rear probe part; 73—microwave emission hole; 74—conduit; 75—laser interface; 76—temperature signal interface; 77—microwave interface.

DETAILED DESCRIPTION OF THE PREFERRED EMBODIMENT

The present invention is further explained in detail with the accompanying drawings.

Figure 2:
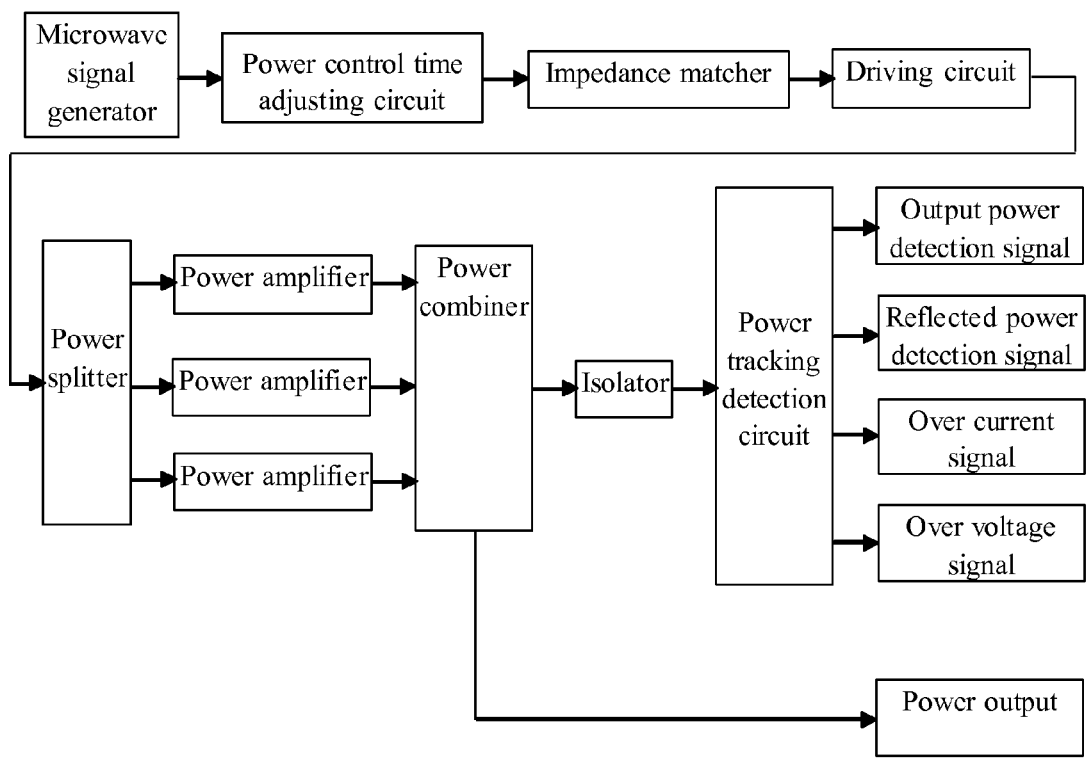
FIG. 2 is a circuit diagram of a microwave generating unit according to the above preferred embodiment of the present invention.
Figure 3:
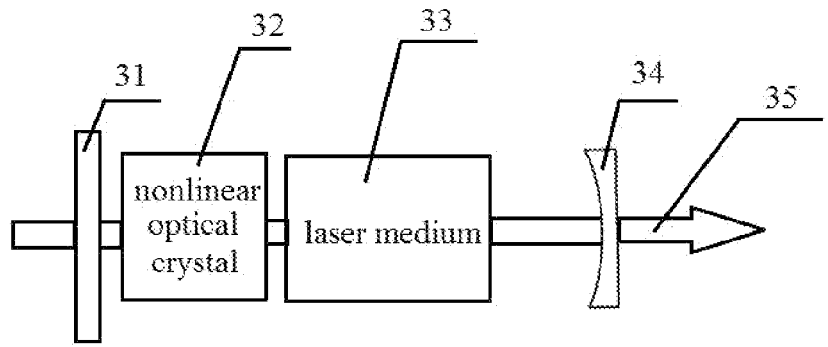
FIG. 3 is a block diagram of a laser generating unit according to the above preferred embodiment of the present invention.
Figure 4:
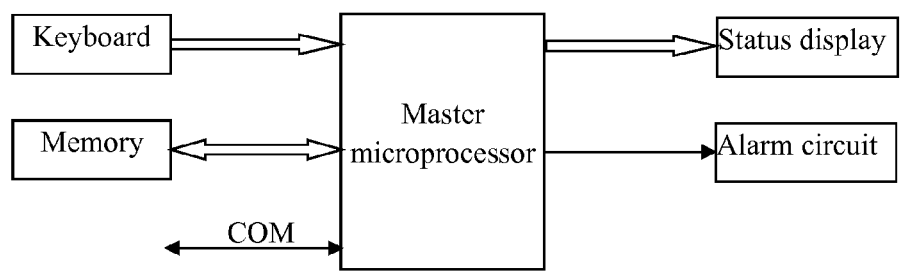
FIG. 4 is a circuit diagram of a microcomputer control unit according to the above preferred embodiment of the present invention.
Figure 5:
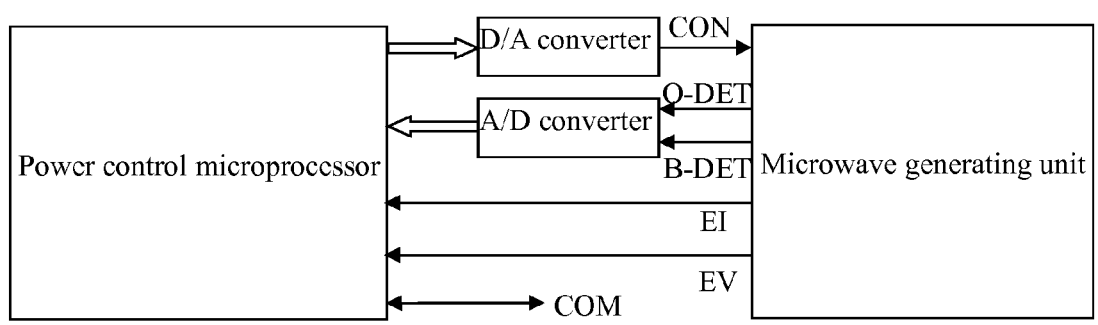
FIG. 5 is a circuit diagram of a power control microprocessor according to the above preferred embodiment of the present invention.
Figure 6:
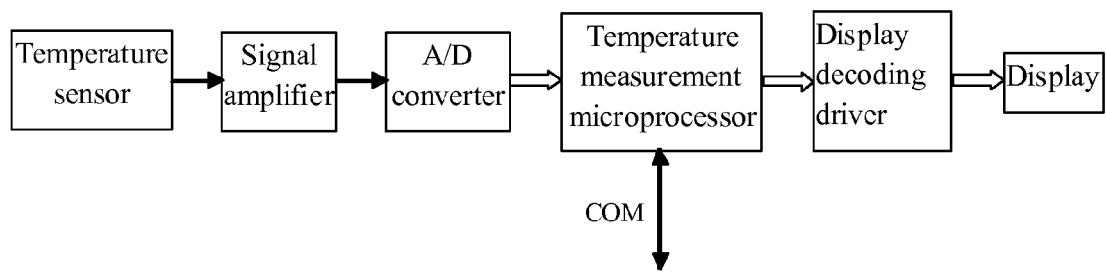
FIG. 6 is a circuit diagram of a temperature measurement microprocessor according to the above preferred embodiment of the present invention.
Figure 7:
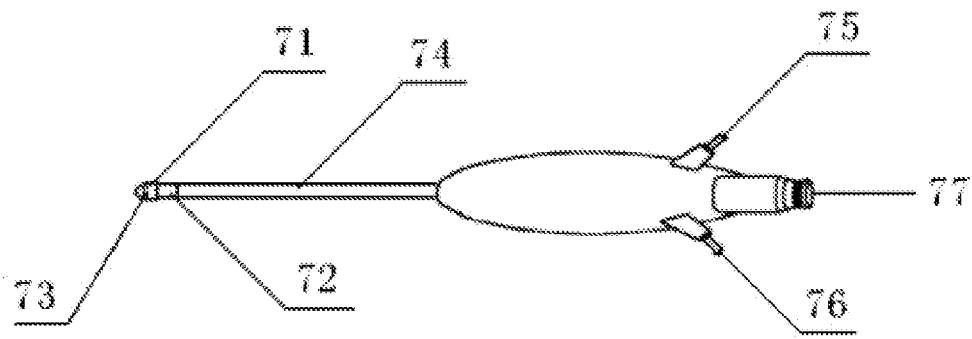
FIG. 7 is a schematic diagram of a microwave radiation probe according to the above preferred embodiment of the present invention.

Referring to FIG. 1 of the drawings, an ultrasonic imaging microwave therapeutic apparatus according to a preferred embodiment of the present invention is illustrated, wherein the ultrasonic imaging microwave therapeutic apparatus comprises a microwave radiation probe (as shown in FIG. 7), a microwave generating unit (as shown in FIG. 2), a laser generating unit (as shown in FIG. 3), a color Doppler ultrasound imaging unit, and a microcomputer control unit (as shown in FIGS. 4-6).

The microwave radiation probe comprises a front probe part 71, a rear probe part 72 and a probe interface part. A microwave emission hole 73 is provided at the front probe part 71. A laser cursor is provided at the rear probe part 72. The rear probe part 72 of the microwave radiation probe has a hollow structure. A wire for the transmission of microwave and a cable for the transmission of laser are provided within the rear probe part 72 of the microwave radiation probe. The rear probe part 72 of the microwave radiation probe is sealedly connected with a conduit 74 having the wire and the cable. The conduit 74 is connected with the probe interface part. A laser interface 75 connected with a port of the laser generating unit and a microwave interface 77 connected with a coaxial output terminal of the microwave generating unit are provided at the probe interface part. A temperature sensor is located within the hollow structure of the rear probe part 72 of the microwave radiation probe. A temperature signal transmission line is located within the conduit 74. A temperature signal interface 76 is provided at the probe interface part.

A power output of the microwave generating unit is connected with the probe interface part to provide a microwave signal for ablation treatment of lower extremity varicose vein. The microwave generating unit comprises a microwave signal generator, a power control time adjusting circuit, an impedance matcher, a driving circuit, a power splitter, a plurality of power amplifiers, a power combiner, an isolator and a power tracking detection circuit. The power tracking detection circuit outputs an output power detection signal, a reflected power detection signal, an over current signal and an over voltage signal.

The laser generating unit, adapted for providing a laser signal which is used to identify a wavelength range of visible light of the microwave probe, comprises an InGaAs infrared laser pump, and a laser cavity. A laser medium 33 and a nonlinear optical crystal 32 are provided within the laser cavity along a same axis. The laser medium 33 is $YVO_4$ crystal doped with $Nd^{3+}$, wherein a doping concentration of $Nd^{3+}$ is 2.5-7.2 at %. The nonlinear optical crystal 32 is KTP crystal.

The color Doppler ultrasound imaging unit, adapted for obtaining the dynamic display of the image of the tissue to be treated and the dynamic display of the image of the tissue while treating, comprises a color Doppler ultrasound host and a color Doppler ultrasound control panel.

The microcomputer control unit outputs a microwave power control signal to control and adjust the power control of the microwave generating unit. The microcomputer control unit outputs a laser control signal to control the switch-on/off of the laser generating unit. The microcomputer control unit comprises a master microprocessor, a power control microprocessor, and a temperature measurement microprocessor, wherein the master microprocessor is connected with the power control microprocessor and the temperature measurement microprocessor via a communication interface COM. The output power detection signal O-DET and the reflected power detection signal B-DET of the microwave generating unit are transformed by an A/D converter, and then sent to the power control microprocessor. The over current signal EI and the over voltage signal EV of the microwave generating unit are inputted into the power control microprocessor. The power control signal CON of the microwave generating unit comes from an output of the D/A converter connecting with the power control microprocessor. According to the value of the output power detection signal, the value of the power control signal is obtained by the power control microprocessor. The reflected power detection signal, the over current signal and the over voltage signal are processed by the power control microprocessor, and then inputted into the master microprocessor by the communication interface, and an alarm circuit is started by the master microprocessor for generating an alarm signal. A temperature signal sensed by the temperature sensor is sent to a signal amplifier. An output of the signal amplifier is transformed by the A/D converter, and then sent to the temperature measurement microprocessor. A temperature value outputted by the temperature measurement microprocessor is displayed by a status display. The master microprocessor is further connected with a keyboard, the status display, the alarm circuit and a memory. The keyboard is adapted for inputting a control instruction to the master microprocessor. The status display is adapted for displaying a working state. The alarm circuit is adapted for generating the alarm signal. The memory is adapted for storing set values and temporary data at work.

The therapeutic apparatus provided by the present invention has been applied to hospitals in Shanghai and treated more than 10000 cases of patients. Now, it is evaluated from the following several aspects based on the beneficial effects of the present invention.

(1) Anesthesia and operation time: an average time of the endovascular microwave coagulation operation time every limb is 15 minutes. The therapeutic apparatus of the present invention has short duration of anesthesia, less anesthetic dosage and rapid recovery.

(2) The intraoperative blood loss is average 2.5 ml.

(3) Postoperative symptom improvement, out of bed activity, the hospitalization time of patients: Patients have not wound and lower limb pains. Only postoperative individual cases have foot temporary mild swelling. Patients can ambulate themselves at 1-2 hours after surgery (or according to anesthesia requirements). The average hospitalization time is 5.3 days.

(4) Changes in appearance of the affected limb: The lower extremity varicose veins disappear, clinical symptoms are obviously improved, limb swelling is reduced, pigmentation is gradually faded, and leg ulcers and skin nutrition disorders are obviously improved or healed.

(5) Complications and recurrence: no deep vein thrombosis, pulmonary embolism or other serious complications occur. Calf skin numbness after the surgery is lighter, the average regression time is 2.5 months, the recurrence rate is lower and about 2% (which is lower than that of other methods).

(6) The postoperative color Doppler ultrasound image of lower extremity venous changes, thus it is proved that the effect is good.

In the immediate patients' postoperative day, the diameter of lower extremity saphenous vein is obviously narrowed, no blood flow displays, it can be seen that the spot, light band and vessel wall having thrombosis strong echo within the lumen are obviously thickened and roughened by two-dimensional ultrasound, and the integrity is destroyed. At two weeks after operation, the intraluminal fibrosis is formed on the foregoing basis, and the interior of the lumen is completely closed.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An ultrasonic imaging microwave therapeutic apparatus, comprising:
    a microwave radiation probe, comprising a front probe part, a rear probe part and a probe interface part, wherein a microwave emission hole is provided at the front probe part, and a laser cursor is provided at the rear probe part;
    a microwave generating unit comprising a microwave generator, wherein a power output of the microwave generating unit is connected with the probe interface part to provide a microwave signal for ablation treatment of lower extremity varicose vein;
    a laser generating unit for providing a laser signal which is used to identify a wavelength range of visible light of the microwave probe;
    a color Doppler ultrasound imaging unit, adapted for obtaining a dynamic display of an image of a tissue to be treated and a dynamic display of an image of a tissue while treating, comprising a color Doppler ultrasound host and a color Doppler ultrasound control panel; and
    a microcomputer control unit, wherein the microcomputer control unit outputs a microwave power control signal to control and adjust a power of the microwave generating unit, the microcomputer control unit outputs a laser control signal to control a switch-on/off of the laser generating unit,
    wherein the microwave generating unit comprises a microwave signal generator, a power control time adjusting circuit, an impedance matcher, a driving circuit, a power splitter, a plurality of power amplifiers, a power combiner, an isolator and a power tracking detection circuit, a microwave signal generated by the microwave signal generator is inputted into the power control time adjusting circuit, an output power is adjusted by the microwave power control signal from the microcomputer control unit and received by the power control time adjusting circuit, an output of the power control time adjusting circuit is connected with the impedance matcher to have an impedance matching for the inputted microwave signal, an output of the impedance matcher is connected with the driving circuit, a signal from the impedance matcher is pre-amplified by the driving circuit and then sent to the power splitter, the power signal is divided into multi-channel signals by the power splitter and then respectively sent to a plurality of power amplifiers for amplifying, the amplified power is synthesized by the power combiner, the synthesized power is outputted by a coaxial output terminal of the isolator, a microwave power output terminal of the isolator is connected with the power tracking detection circuit.

2. The ultrasonic imaging microwave therapeutic apparatus, as recited in claim 1, wherein the power tracking detection circuit outputs an output power detection signal, a reflected power detection signal, an over current signal and an over voltage signal.

3. The ultrasonic imaging microwave therapeutic apparatus, as recited in claim 2, wherein the laser generating unit comprises an InGaAs infrared laser pump, and a laser cavity, wherein a laser medium and a nonlinear optical crystal are provided within the laser cavity along a same axis, the laser medium is YVO4 crystal doped with Nd3+, wherein a doping concentration of Nd3+ is 2.5-7.2at %, and the nonlinear optical crystal is KTP crystal.

4. The ultrasonic imaging microwave therapeutic apparatus, as recited in claim 2, wherein the rear probe part of the microwave radiation probe has a hollow structure, a wire for a transmission of microwave and a cable for a transmission of laser are provided within the rear probe part of the microwave radiation probe, the rear probe part of the microwave radiation probe is sealedly connected with a conduit having the wire and the cable, the conduit is connected with the probe interface part, a laser interface connected with a port of the laser generating unit and a microwave interface connected with a coaxial output terminal of the microwave generating unit are provided at the probe interface part.

5. The ultrasonic imaging microwave therapeutic apparatus, as recited in claim 4, wherein a temperature sensor is located within the hollow structure of the rear probe part of the microwave radiation probe, a temperature signal transmission line is located within the conduit, and a temperature signal interface is provided at the probe interface part.

6. The ultrasonic imaging microwave therapeutic apparatus, as recited in claim 5, wherein the microcomputer control unit comprises a master microprocessor, a power control microprocessor, and a temperature measurement microprocessor, wherein the master microprocessor is connected with the power control microprocessor and the temperature measurement microprocessor via a communication interface.

7. The ultrasonic imaging microwave therapeutic apparatus, as recited in claim 6, wherein the output power detection signal and the reflected power detection signal of the microwave generating unit are transformed by an A/D converter, and then sent to the power control microprocessor, the over current signal and the over voltage signal of the microwave generating unit are inputted into the power control microprocessor, a power control signal of the microwave generating unit comes from an output of the D/A converter connecting with the power control microprocessor, a value of the power control signal is obtained by the power control microprocessor according to a value of the output power detection signal, the reflected power detection signal, the over current signal and the over voltage signal are processed by the power control microprocessor, and then inputted into the master microprocessor via the communication interface, and an alarm circuit is started by the master microprocessor for generating an alarm signal.

8. The ultrasonic imaging microwave therapeutic apparatus, as recited in claim 7, wherein a temperature signal sensed by the temperature sensor is sent to a signal amplifier, an output of the signal amplifier is transformed by the A/D converter, and then sent to the temperature measurement microprocessor, a temperature value outputted by the temperature measurement microprocessor is displayed by a status display.

9. The ultrasonic imaging microwave therapeutic apparatus, as recited in claim 8, wherein the master microprocessor is further connected with a keyboard, the status display, the alarm circuit and a memory.

10. The ultrasonic imaging microwave therapeutic apparatus, as recited in claim 5, wherein the output power detection signal and the reflected power detection signal of the microwave generating unit are transformed by an A/D converter, and then sent to the power control microprocessor, the over current signal and the over voltage signal of the microwave generating unit are inputted into the power control microprocessor, a power control signal of the microwave generating unit comes from an output of the D/A converter connecting with the power control microprocessor, a value of the power control signal is obtained by the power control microprocessor according to a value of the output power detection signal, the reflected power detection signal, the over current signal and the over voltage signal are processed by the power control microprocessor, and then inputted into the master microprocessor via the communication interface, and an alarm circuit is started by the master microprocessor for generating an alarm signal.

11. The ultrasonic imaging microwave therapeutic apparatus, as recited in claim 1, wherein the laser generating unit comprises an InGaAs infrared laser pump, and a laser cavity, wherein a laser medium and a nonlinear optical crystal are provided within the laser cavity along a same axis, the laser medium is YVO4 crystal doped with Nd3+, wherein a doping concentration of Nd3+ is 2.5-7.2at %, and the nonlinear optical crystal is KTP crystal.

12. The ultrasonic imaging microwave therapeutic apparatus, as recited in claim 1, wherein the rear probe part of the microwave radiation probe has a hollow structure, a wire for a transmission of microwave and a cable for a transmission of laser are provided within the rear probe part of the microwave radiation probe, the rear probe part of the microwave radiation probe is sealedly connected with a conduit having the wire and the cable, the conduit is connected with the probe interface part, a laser interface connected with a port of the laser generating unit and a microwave interface connected with a coaxial output terminal of the microwave generating unit are provided at the probe interface part.

13. The ultrasonic imaging microwave therapeutic apparatus, as recited in claim 12, wherein a temperature sensor is located within the hollow structure of the rear probe part of the microwave radiation probe, a temperature signal transmission line is located within the conduit, and a temperature signal interface is provided at the probe interface part.

14. The ultrasonic imaging microwave therapeutic apparatus, as recited in claim 13, wherein the microcomputer control unit comprises a master microprocessor, a power control microprocessor, and a temperature measurement microprocessor, wherein the master microprocessor is connected with the power control microprocessor and the temperature measurement microprocessor via a communication interface.

15. An ultrasonic imaging microwave therapeutic apparatus, comprising:
  a microwave radiation probe, comprising a front probe part, a rear probe part and a probe interface part, wherein a microwave emission hole is provided at the front probe part, and a laser cursor is provided at the rear probe part;
  a microwave generating unit comprising a microwave generator, wherein a power output of the microwave generating unit is connected with the probe interface part to provide a microwave signal for ablation treatment of lower extremity varicose vein;
  a laser generating unit for providing a laser signal which is used to identify a wavelength range of visible light of the microwave probe;
  a color Doppler ultrasound imaging unit, adapted for obtaining a dynamic display of an image of a tissue to be treated and a dynamic display of an image of a tissue while treating, comprising a color Doppler ultrasound host and a color Doppler ultrasound control panel; and
  a microcomputer control unit, wherein the microcomputer control unit outputs a microwave power control signal to control and adjust a power of the microwave generating unit, the microcomputer control unit outputs a laser control signal to control a switch-on/off of the laser generating unit, wherein the laser generating unit comprises an InGaAs infrared laser pump, and a laser cavity, wherein a laser medium and a nonlinear optical crystal are provided within the laser cavity along a same axis, the laser medium is YVO4 crystal doped with Nd3+, wherein a doping concentration of Nd3+ is 2.5-7.2at %, and the nonlinear optical crystal is KTP crystal.

16. An ultrasonic imaging microwave therapeutic apparatus, comprising:

a microwave radiation probe, comprising a front probe part, a rear probe part and a probe interface part, wherein a microwave emission hole is provided at the front probe part, and a laser cursor is provided at the rear probe part;

a microwave generating unit comprising a microwave generator, wherein a power output of the microwave generating unit is connected with the probe interface part to provide a microwave signal for ablation treatment of lower extremity varicose vein;

a laser generating unit for providing a laser signal which is used to identify a wavelength range of visible light of the microwave probe;

a color Doppler ultrasound imaging unit, adapted for obtaining a dynamic display of an image of a tissue to be treated and a dynamic display of an image of a tissue while treating, comprising a color Doppler ultrasound host and a color Doppler ultrasound control panel; and a microcomputer control unit, wherein the microcomputer control unit outputs a microwave power control signal to control and adjust a power of the microwave generating unit, the microcomputer control unit outputs a laser control signal to control a switch-on/off of the laser generating unit, wherein the rear probe part of the microwave radiation probe has a hollow structure, a wire for a transmission of microwave and a cable for a transmission of laser are provided within the rear probe part of the microwave radiation probe, the rear probe part of the microwave radiation probe is sealedly connected with a conduit having the wire and the cable, the conduit is connected with the probe interface part, a laser interface connected with a port of the laser generating unit and a microwave interface connected with a coaxial output terminal of the microwave generating unit are provided at the probe interface part, wherein a temperature sensor is located within the hollow structure of the rear probe part of the microwave radiation probe, a temperature signal transmission line is located within the conduit, and a temperature signal interface is provided at the probe interface part, wherein the microcomputer control unit comprises a master microprocessor, a power control microprocessor, and a temperature measurement microprocessor, wherein the master microprocessor is connected with the power control microprocessor and the temperature measurement microprocessor via a communication interface.

17. An ultrasonic imaging microwave therapeutic apparatus, comprising:

a microwave radiation probe, comprising a front probe part, a rear probe part and a probe interface part, wherein a microwave emission hole is provided at the front probe part, and a laser cursor is provided at the rear probe part;

a microwave generating unit comprising a microwave generator, wherein a power output of the microwave generating unit is connected with the probe interface part to provide a microwave signal for ablation treatment of lower extremity varicose vein;

a laser generating unit for providing a laser signal which is used to identify a wavelength range of visible light of the microwave probe;

a color Doppler ultrasound imaging unit, adapted for obtaining a dynamic display of an image of a tissue to be treated and a dynamic display of an image of a tissue while treating, comprising a color Doppler ultrasound host and a color Doppler ultrasound control panel; and a microcomputer control unit, wherein the microcomputer control unit outputs a microwave power control signal to control and adjust a power of the microwave generating unit, the microcomputer control unit outputs a laser control signal to control a switch-on/off of the laser generating unit, wherein the rear probe part of the microwave radiation probe has a hollow structure, a wire for a transmission of microwave and a cable for a transmission of laser are provided within the rear probe part of the microwave radiation probe, the rear probe part of the microwave radiation probe is sealedly connected with a conduit having the wire and the cable, the conduit is connected with the probe interface part, a laser interface connected with a port of the laser generating unit and a microwave interface connected with a coaxial output terminal of the microwave generating unit are provided at the probe interface part, wherein the microwave radiation probe is a single-use microwave radiation probe, a unique identification code chip is located within the hollow structure of the rear probe part of the microwave radiation probe, the unique identification code chip is connected with the microcomputer control unit by the communication interface, the microcomputer control unit judges whether the microwave radiation probe is used by the unique identification code sensor.

* * * * *